United States Patent [19]
Buix et al.

[11] 3,971,629
[45] July 27, 1976

[54] RETORTING TRAY

[75] Inventors: Louis F. Buix, Crystal Lake; Harry J. Gribnitz, Addison; Gary A. Hohner, Sleepy Hollow, all of Ill.

[73] Assignee: The Quaker Oats Company, Chicago, Ill.

[22] Filed: Feb. 3, 1975

[21] Appl. No.: 546,610

[52] U.S. Cl. ................................ 21/105; 21/78; 34/238; 99/369; 99/417; 99/467; 99/483; 211/126; 211/135
[51] Int. Cl.² .................... A61L 3/02; A23L 3/10
[58] Field of Search .............. 21/83, 105; 34/238; 211/126, 127, 135; 99/369, 467, 417, 415, 483; 108/25

[56] References Cited
UNITED STATES PATENTS

| | | |
|---|---|---|
| 1,526,005 | 2/1925 | McKenzie ............................ 34/238 |
| 2,487,584 | 11/1949 | Patterson ....................... 211/135 X |
| 2,879,886 | 3/1959 | Crane ................................. 211/126 |
| 3,403,788 | 10/1968 | Kreeger ............................. 211/126 |
| 3,454,189 | 7/1969 | Lauterbach ........................... 21/56 |

*Primary Examiner*—Morris O. Wolk
*Assistant Examiner*—Dale Lovercheck
*Attorney, Agent, or Firm*—Charles J. Hunter

[57] ABSTRACT

A retorting tray for sterilizing material sealed in flexible pouches. The tray comprises a base portion which forms a conduit for circulation of a heating medium therethrough. The base portion has edges extending therefrom terminating in a stackable feature whereby one tray can stack on the other. The base also has protuberances therefrom for spacing apart the flexible pouches in a substantially unmovable manner to control the maximum cross-section of the pouch and for providing a space for circulation of a heating medium about the flexible pouches to sterilize the contents.

9 Claims, 4 Drawing Figures

RETORTING TRAY

BACKGROUND OF THE INVENTION

1. Field of the Invention

This invention relates to a tray for placing flexible pouches containing food or other items on the tray and retort sterilizing the items in the flexible pouches.

2. Description of the Prior Art

Recent discoveries have made possible the sealing of food products in air and light impermeable flexible containers which can then be retorted to sterilize the food products therein. This method is becoming increasingly accepted as a highly desirable food preservation system. In the past, the food in such pouches have been cooked by clamping the top of the pouches individually and placing them in a large retort device. This prior procedure has proved to be time consuming and inefficient for a large volume operation. The tray of this invention can be used to provide a method of stacking such pouches and placing them in large quantities in a retort device for sterilization of the food therein. In addition, manually sliding pouches into vertical slots in a retort rack has the disadvantage of physical damage during loading and the additional labor and time required.

Still additionally, prior known designs of trays do not provide for controlled cross-sectional area of exposure of the pouches thereby not permitting an accurate design of the sterilization process based on a known and controlled heat penetration rate.

Other prior methods for sterilizing material in flexible pouches include vertically spaced slots in racks which are difficult to load manually and nearly impossible to automatically load. Other methods include flat trays which are difficult to load automatically and which do not allow for positive control of water flow through the conduit between pouch layers. Still other prior methods include individual, separate pockets to support and confine the pouch but these are expensive and difficult to load and unload.

SUMMARY OF THE INVENTION

It is an object of this invention to provide a tray for use in the retort sterilization of food sealed in flexible pouches.

It is a further object of this invention to provide a system which in combination provides for the placement of food containing flexible pouches in a heating medium whereby the food in the flexible pouches can be sterilized.

It is a further object of this invention to provide a tray which can be easily loaded and unloaded, either manually or automatically, with the pouch and tray horizontal.

It is still another object of this invention to provide a tray for holding pouches while a heating medium circulates thereabout which provides for a positive control of pouch thickness and spacing.

It is an additional object of this invention to provide a tray for holding pouches which provides for an uninterrupted flow of a heating medium about the pouch and with the pouches easily oriented in the formed conduits.

The objects of this invention are accomplished by a tray for use in the retort sterilization of sealed flexible pouches containing food or other items, said tray comprising a bottom portion comprising a conduit for circulating a heating medium therethrough, edge walls projecting outward from opposing sides of the bottom portion and terminating in wall ends engageable with the bottom portion of a like tray and protuberances porjecting outward from the bottom portion to space apart flexible pouches on the tray to control the exposed cross-section of the pouches and prevent substantial movement of the pouches on the tray, said protuberances being sufficiently open to allow for circulation of a heating medium about the trays.

Preferably in the above, the tray has a substantially rectangular base and the protuberances are a plurality of curved loops.

The objects of this invention are further accomplished by the combination comprising a plurality of stacked trays held together with spaced apart substantially unmovable sealed flexible pouches having an item to be sterilized therein, said trays having a continuous conduit therethrough for circulation of a heating medium, and said flexible pouches being spaced apart in formed cavities creating a continuous conduit for circulation of a heating medium about the entire outer surfaces of the flexible pouches.

In the tray of this invention the bottom and top portions thereof form stackable features, that is, one of the portions will fit snugly inside the other portion so that the trays may engage one another or stack one upon the other. The base of the trays provides a conduit for the circulation of a heating medium such as heated water or steam or the like and provides for a clear conduit for the heating medium other than that conduit containing the flexible pouches which may have the transfer of the heating medium somewhat obstructed by the location of the pouches therein. The base of the tray also has protuberances extending therefrom with the protuberances not substantially blocking the circulation of the heating medium and providing for accurate control of the maximum pouch cross-section to allow for accurate and controlled uniform sterilization of all portions of the pouch, and with the protuberances providing somewhat for the substantial holding of the pouches in place, that is, for preventing the pouches from bunching together at one end of the tray or moving substantially about the tray and with sometimes the desirable feature of the protuberances additionally being used to support the bottom surface of the tray stacked above the particular tray having the protuberances thereon. Flexible pouches containing food material are placed in the trays and these are in turn stacked in a bin open ended on each end which provides for the circulation of a heating medium about the pouches thereby sterilizing the item contained in the pouches.

BRIEF DESCRIPTION OF THE DRAWINGS

This invention may be more fully described but is not limited by the attached drawings wherein.

Figure 1:
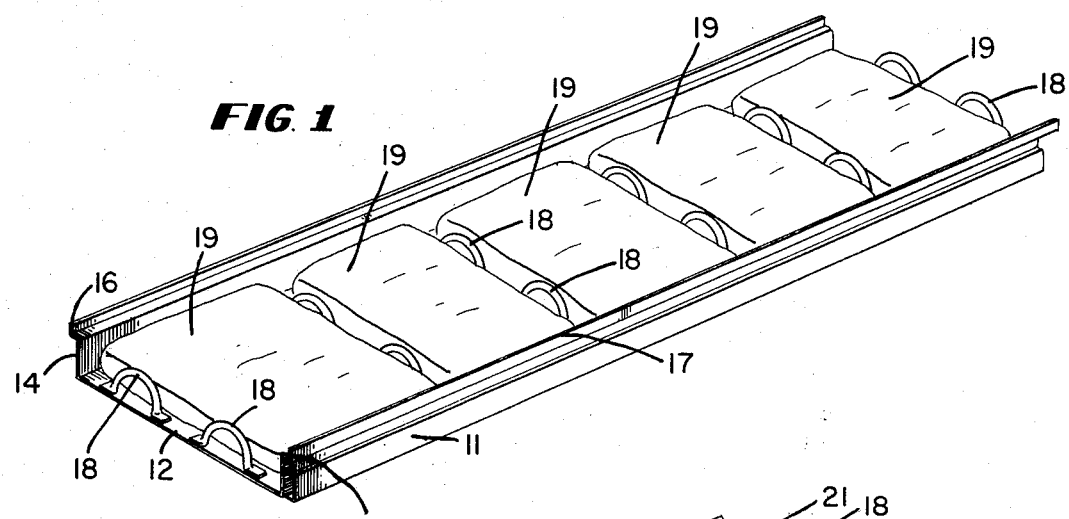
FIG. 1 is a perspective view of the tray of this invention having the flexible pouches thereon.
Figure 2:
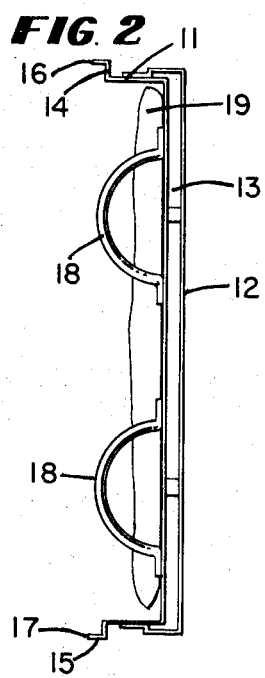
FIG. 2 is an end view of the tray of this invention having the flexible pouches thereon.
Figure 4:
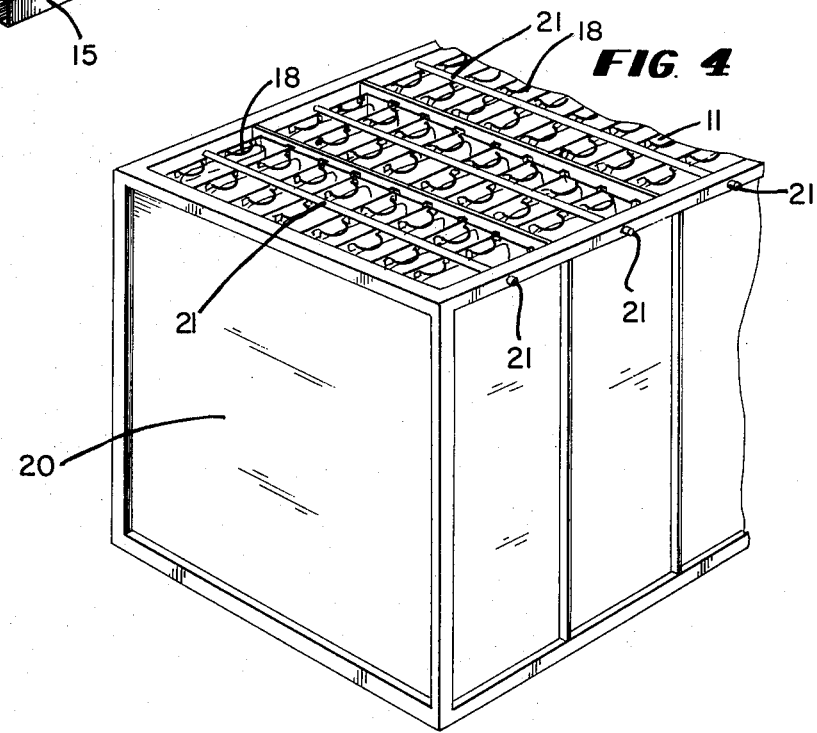
FIG. 4. is a perspective view of an open ended bin containing a plurality of the stacked trays.
Figure 3:
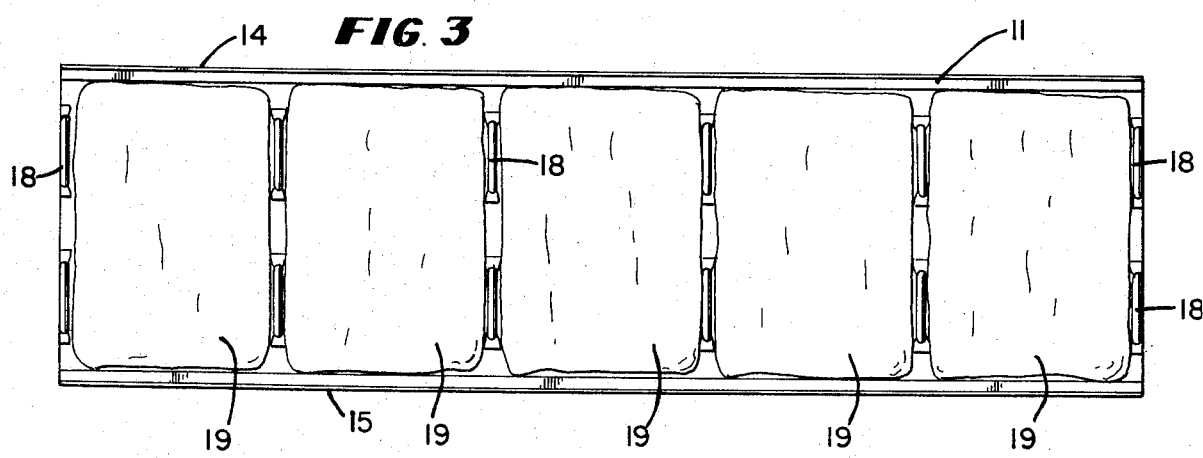
FIG. 3 is a top view of the tray of this invention having flexible pouches thereon.

In the drawings, numeral 11 refers to the tray of this invention. The tray 11 has a base 12 which is formed as a conduit 13 which is useful in the circulation of a heating medium therethrough. The base has side extensions 14 and 15 projecting outward therefrom and terminating in wall ends 16 and 17 engageable with the bottom portion of the like tray. In this case, the wall ends are bent outward and upward so that they fit snugly around the bottom of a tray stacked thereon and engage it. Also extending outward from the base are a plurality of protuberances 18 which accurately control the exposed cross-section of flexible pouches 19 and hold them in place while also providing a conduit for a heating medium to flow about the flexible pouches. The stacked trays with the pouches thereon are placed in a heating bin 20, open on two ends for the circulation of a heating medium, and the trays are restrained from moving out of the bin by restraining bars 21.

In operation the flexible pouches are stacked between the protuberances on the tray, the trays are stacked in the bin with restraining bars then placed to keep the trays from moving, and a heating medium is circulated through the conduit in the tray and about the flexible pouches to provide sterilization of the food in the flexible pouches. Common heating mediums are those employed in large retort cookers available in the canning industry. The protuberances on the trays may be any type of protuberance which can space apart the flexible pouches, although hereshown is a curved loop which provides a very efficient design for both passing a heating medium therethrough without obstruction and for spacing apart the pouches to prevent lateral movement thereof in the tray. Also, while it may be recognized that many different designs and shapes of trays are acceptable within the scope of this invention, it is particularly acceptable to use the rectangular shaped base herein described. Also, while a multiplicity of designs may be available for providing the stacking feature of the termination of the edges of the tray of this invention, it has been shown herein to use an outward and upward design although other recognized designs may be acceptable within the scope of this invention.

DESCRIPTION OF THE PREFERRED EMBODIMENTS

The drawings attached hereto represent the preferred embodiments of this invention. It may be seen that many modifications of this design may still be acceptable within the scope of this invention, however, and it is intended to claim herein those modifications which fit the inventive concept disclosed herein.

It may thus be seen that this invention provides a new and novel design for a tray for sterilizing food containing flexible pouches in a systemmatic manner. If other types of designs are used, they are cumbersome and labor consuming and do not provide a good sterilization process. If still other designs are used, they do not provide for the spacing apart of the flexible pouches, that is, the flexible pouches are bunched together and thereby hot spots and unsterilized spots are created which does not provide uniform quality in the cooked product. Additionally, if further processes and designs are used, the heating medium does not circulate about the flexible pouches to the extent necessary to provide even sterilization. In this new and novel design the heating medium can provide even sterilization by having a guaranteed path next to each of the pouches by its passage through the conduit formed in the base of the tray. In addition, the heating medium can be circulated about each of the flexible pouches by passing through the conduit formed by the stackable trays with the pouches therein. Still further in addition, the tray of this invention provides for accurate control of the heating of the material in the pouches by providing for accurate determination of the heat transfer by known methods. It may thus be seen that this new and novel invention provides a new and unique system for sterilizing items in flexible pouches.

Having fully described this new and unique invention, the following is claimed:

1. A tray for use in the retort sterilization of material contained in sealed flexible pouches, said tray comprising:
   a. An elongated bottom;
   b. Two elongated sidewalls extending upwards from opposite sides of said bottom;
   c. Said sidewalls terminating in nesting means for stacking a plurality of like trays in a nesting configuration;
   d. Two narrow ends at opposite ends of said bottom and at a right angle to said side-walls, said narrow ends being open;
   e. Protuberances extending upwards from the bottom to space apart flexible pouches on the tray and to control the maximum cross section of the pouch during sterilization to insure complete, uniform and accurate heat penetration and sterilization of the contents of the pouch and to prevent substantial movement of the pouches on the tray, said protuberances being sufficiently open to allow for circulation of a heating medium about the trays;
   f. Conduit means for circulating a heating medium around the bottom and the side-walls, said conduit means being attached to the sidewalls of the tray and partially surrounding said tray on three sides.

2. A tray as in claim 1, wherein the conduit means comprises a rectangular panel having a base and two elongated arms along the length of the panel, each arm extending upwardly from opposite sides of said panel base, each of said arms being attached to the tray along the elongated side-walls, thereby providing a clearance between the tray bottom and said panel as well as a clearance between each of said side-walls and said panel.

3. A tray as in claim 2, wherein said tray is a lower tray and the nesting means comprises a first L-shaped structure and a second L-shaped structure, said first L-shaped structure having one end mounted on said first side-wall and the other end extending generally upwards, said second L-shaped structure having one end mounted on said second side-wall and the other end extending generally upwards, said nesting means being engageable with the base of an upper tray which has a structure identical to that of the lower tray so that the upper tray can be slid across the lower tray laterally to a stacked or nested position by engaging the nesting means of the lower tray with the base of the upper tray, said nesting means thereby maintaining an open space between the trays.

4. The tray defined in claim 3, wherein said protuberances each comprise an inverted generally U-shaped frame attached to the bottom of said tray and having downwardly diverging legs.

5. A tray for use in the retort sterilization of material contained in sealed flexible pouches, said tray comprising: a bottom portion; first and second side-walls projected outward from opposing sides of the bottom portion and terminating in wall ends engageable with a base panel of a like tray; a conduit for circulating a heting medium therethrough, said conduit comprising a rectangular base panel and two elongated side panels each side panel extending upwardly along the length of the base panel from opposite sides of said base panel, each of said side panels being attached to the tray along a line on the elongated side-walls, said line being spaced upwardly apart from said bottom portion thereby providing a clearance between each of said side-walls and said respective side panels; and protuberances projecting outward from the bottom portion to space apart flexible pouches on the tray and to control the maximum cross-section of the pouch during sterilization to insure complete, uniform and accurate heat penetration and sterilization of the contents of the pouch and to prevent substantial movement of the pouches on the tray, said protuberances being sufficiently open to allow for circulation of a heating medium about the trays.

6. A tray as in claim 5 which has a substantially rectangular base and wherein the protuberances are a plurality of curved loops.

7. A tray for use in the retort sterilization of material contained in sealed flexible pouches, said tray comprising:
   a. an elongated U-shaped inner tray having an elongated base, a first elongated side-wall, a second elongated side-wall and two narrow ends;
   b. an elongated U-shaped outer panel having two elongated arms, said U-shaped panel partially surrounding said U-shaped tray on at least three sides and being attached to the tray on at least two sides, thereby providing a bottom clearance between the tray base and said panel as well as side clearance between each of the said side-walls and said panel;
   c. nesting means attached to said U-shaped container;
   d. protuberances extending upwards from the base to space apart flexible pouches on the tray and to control the maximum cross-section of the pouch during sterilization to insure complete, uniform and accurate heat penetration and sterilization of the contents of the pouch and to prevent substantial movement of the pouches on the tray, said protuberances and said clearances being sufficiently open to allow for circulation of a heating medium therethrough about the tray.

8. A tray as in claim 7, wherein said tray is a lower tray and the nesting means comprises a first L-shaped structure and a second L-shaped structure, said first L-shaped structure having one end mounted on said first side-wall and the other end extending generally upwards, said second L-shaped structure having one end mounted on said second side-wall and the other engageable with the base of an upper tray which has a structure identical to that of the lower tray so that the upper tray can be slid across the lower tray laterally to a stacked or nested position by engaging the nesting means of the lower tray with the base of the upper tray, said nesting means thereby maintaining an open space between the trays.

9. The tray defined in claim 8, wherein said protuberances each comprise an inverted generally U-shaped frame attached to the base of said tray and having downwardly diverging legs.

* * * * *

UNITED STATES PATENT OFFICE
CERTIFICATE OF CORRECTION

PATENT NO. : 3,971,629
DATED : July 27, 1976
INVENTOR(S) : Louis F. Buix, Harry J. Gribnitz, Gary A. Hohner It is certified that error appears in the above-identified patent and that said Letters Patent are hereby corrected as shown below:

Column 2, Line 5, "porjecting" should read --projecting--

In Claim 5, at Column 5, Line 1, "heting" should read --heating--.

In Claim 8, at Column 6, Line 22, insert after other and before engageable, --end extending generally upwards, said nesting means being--.

Signed and Sealed this

Twenty-eighth Day of December 1976

[SEAL]

Attest:

RUTH C. MASON
Attesting Officer

C. MARSHALL DANN
Commissioner of Patents and Trademarks